(12) United States Patent
Lal et al.

(10) Patent No.: US 6,503,708 B1
(45) Date of Patent: Jan. 7, 2003

(54) MICROTUBULE-ASSOCIATED PROTEIN

(75) Inventors: Preeti Lal, Santa Clara, CA (US); Neil C. Corley, Mountain View, CA (US)

(73) Assignee: Incyte Genomics, Inc., Palo Alto, CA (US)

(*) Notice: Subject to any disclaimer, the term of this patent is extended or adjusted under 35 U.S.C. 154(b) by 0 days.

(21) Appl. No.: 09/013,118

(22) Filed: Jan. 26, 1998

(51) Int. Cl.[7] ............................ C12Q 1/68; C12P 21/06; C12N 15/00; C12N 1/20; C07H 21/04
(52) U.S. Cl. ...................... 435/6; 435/69.1; 435/252.3; 435/320.1; 435/325; 536/23.1; 536/24.5
(58) Field of Search .................... 536/23.1, 24.5; 435/69.1, 252.3, 320.1, 6, 325

(56) References Cited

PUBLICATIONS

Lehninger, "Biochemistry" 1975 Worth Publishers p. 962.*
1993/94 New England Biolabs Catalog pp. 152–153.*
Genebank Accession No.: T26646 Oct. 16, 1996.*
Genebank Accession No.: AA173577 Dec. 26, 1996.*
Genebank Accession No.: AA278788 Aug. 15, 1997.*
Lazar et al, "Transforming Growth Factor Alpha: Mutation of Aspartic Acid 47 and Leucine 48 Results in Different Biological Activities", Molecular and Cellular biol., vol. 8, No. 3, pp. 1247–1252, Mar. 1988.*
Burgess et al, "Possible dissociation of the Heparin–binding and Mitogenic Activities of Heparin–binding Growth Factor–1 from its Receptor–binding Activities by Site–directed Mutagenesis of a Single Lysine Residue", J. of Celular Biol., vol. 111, pp. 2129, Nov. 1990.*
Bowie et al, "Deciphering the Message in Protein Sequences: Tolerance to Amino Acid Substitutions", Science, vol. 247, pp. 1306–1310, Mar. 1990.*
Reiger et al, Glossary of Genetics and Cytogenetics, 4th Ed., pp. 17–18, 1976.*
Bork, P. "Power and Pitfalls in Sequence Analysis: the 70% Hurdle", Genome research, vol. 10, pp. 398–400, 2000.*
Alberts et al, Ed., Molecular Biology of the Cell (textbook), 3rd edition, p. 465, 1994.*
Shantz and Pegg, "Translational regulation of ornithine decarboxylase and other enzymes", International J of Beiochemistry and Cell Biology, vol. 31, pp. 107–122, 1999.*
McClean and Hill, "Evidence of post–translational regulation of p–glycoprotein", European J. of Cancer, vol. 29A, pp. 2243–2248, 1993.*
Fu et al, "Translational regulation of human p53 gene expression", EMBO, vol. 15, pp. 4392–4401, 1996.*
Mathews and Van Holde, Biochemistry (textbook), 2nd edition, pp. 165–171, 1996.*
B. Matthews, "Genetic and Structural analysis of the protein stability problem", in Perspectives in Biochemistry, vol. 1, pp. 6–9, 1989.*
Ding, M. And Vandre, D., "High Molecular Weight Microtubule–associated Proteins Contain O–Linked N–Acetylglucosamine," *The Journal of Biological Chemistry*, 271(21):12555–12561 (1996).
Hasegawa, M., et al., "Alzheimer–like Changes in Microtubule–associated Protein Tau Induced by Sulfated Glycosaminoglycans," *The Journal of Biological Chemistry*, 272(52):33118–33124 (1997).
Matsumoto, S. And Yahara, I., (GI 1928989), GenBank Sequence Database (Accession U92821), National Center for Biotechnology Information, National Library of Medicine, Bethesda, Maryland 20894 Apr. 1, 1997.
Matsumoto, S. And Yahara, I., (GI 1928988), GenBank Sequence Database (Accession U92821), National Center for Biotechnology Information, National Library of Medicine, Bethesda, Maryland 20894 Apr. 6, 1997.

* cited by examiner

Primary Examiner—Anthony C. Caputa
Assistant Examiner—Karen A. Canella
(74) Attorney, Agent, or Firm—Incyte Genomics, Inc.

(57) ABSTRACT

The invention provides a human microtubule-associated protein (HMAP) and polynucleotides which identify and encode HMAP. The invention also provides expression vectors, host cells, antibodies, agonists, and antagonists. The invention also provides methods for treating or preventing disorders associated with expression of HMAP.

10 Claims, 10 Drawing Sheets

```
                                                              54
5' NNT AGA AGG GCA ACC TCG TGC TTT CTG CAG AGG AGA CCG GAG GGC AGA AGG CAG
     9        18        27        36        45          108
AGT CCA GGC TTA GAC TGC AGT TCC TCG CTT ACC TGT GCA GTC TAA TTT TGA GCT
    63        72        81        90        99          162
GCC TCT TTG TAG TCT TAA AAG GCA GGA GCT TCG TGT TGT GGG TCT GCT AAC CCG
   117       126       135       144       153          216
TAC GTT TCC GTG GGC AAG TCG TGT GTA CTC CTC GCC ATG GCT CAG CTC CAA ACA T
   171       180       189       198       207       M   A   Q   L   Q   T
                                                              270
CGC TTC TAC ACT GAT AAC AAG AAA TAT GCC GTA GAT GAT GTT CCC TTC TCA ATC
 R   F   Y   T   D   N   K   K   Y   A   V   D   D   V   P   F   S   I
225       234       243       252       261                    324
CCT GCT GCC TCT GAA ATT GCC GAC CTT AGT AAC ATC ATC AAT CTA CTA AAG
 P   A   A   S   E   I   A   D   L   S   N   I   I   N   K   L   L   K
279       288       297       306       315                    378
GAC AAA AAT GAG TTC CAC AAA CAT GTG GAG TTT GAT TTC CTT ATT AAG GGC CAG
 D   K   N   E   F   H   K   H   V   E   F   D   F   L   I   K   G   Q
333       342       351       360       369
```

FIGURE 1A

| 387 | | | | | 396 | | | 405 | | 414 | | 423 | | | 432 |
|---|---|---|---|---|---|---|---|---|---|---|---|---|---|---|---|
| TTT | CTG | CGA | ATG | CCC | TTG | GAC | AAA | CAC | ATG | GAA | AAC | GTC | TCA | TCA | GAA |
| F | L | R | M | P | L | D | K | H | M | E | N | V | S | S | E |

| 441 | | | | | 450 | | | 459 | | 468 | | 477 | | | 486 |
|---|---|---|---|---|---|---|---|---|---|---|---|---|---|---|---|
| GAA | GTT | GAA | ATA | GAA | TAC | GTG | AAG | GAG | TAT | ACT | GCA | CCC | CAG | CCA | CAA |
| E | V | E | I | E | Y | V | K | E | Y | T | A | P | Q | P | Q |

| 495 | | | | | 504 | | | 513 | | 522 | | 531 | | | 540 |
|---|---|---|---|---|---|---|---|---|---|---|---|---|---|---|---|
| TGC | ATG | TTC | CAT | GAT | GAC | TGG | ATC | AGT | TCA | ATT | AAA | GGG | GCA | GAG | ATC |
| C | M | F | H | D | D | W | I | S | S | I | K | G | A | E | I |

| 549 | | | | | 558 | | | 567 | | 576 | | 585 | | | 594 |
|---|---|---|---|---|---|---|---|---|---|---|---|---|---|---|---|
| TTG | ACT | GGT | TCT | TAT | GAT | AAG | ACT | TCT | CGG | ATC | TGG | TCC | TTG | GAA | TCA |
| L | T | G | S | Y | D | K | T | S | R | I | W | S | L | E | S |

| 603 | | | | | 612 | | | 621 | | 630 | | 639 | | | 648 |
|---|---|---|---|---|---|---|---|---|---|---|---|---|---|---|---|
| ATA | ATG | ACA | ATT | GTG | GGA | CAT | ACG | GAT | GTT | GTA | AAA | GAT | GTG | GCC | AAA |
| I | M | T | I | V | G | H | T | D | V | V | K | D | V | A | K |

| 657 | | | | | 666 | | | 675 | | 684 | | 693 | | | 702 |
|---|---|---|---|---|---|---|---|---|---|---|---|---|---|---|---|
| AGT | GAT | AGT | TTG | TCC | TGC | TTA | TTA | TTG | AGT | GCT | TCT | ATG | GAT | CAG | ACT | ATT | CTC |
| S | D | S | L | S | C | L | L | L | S | A | S | M | D | Q | T | I | L |

```
     711             720             729             738             747             756
TTA  TGG  GAG  TGG  AAT  GTA  GAG  AGA  AAC  AAA  GTG  GCC  CTA  CAC  TGC  TGT  AGA
 L    W    E    W    N    V    E    R    N    K    V    A    L    H    C    C    R 765             774             783             792             801             810
GGT  CAT  GCT  GGA  AGT  GAT  GTA  GAT  TCT  ATA  GCT  GTT  GGA  TCA  GGA  ACT  AAA  TTT
 G    H    A    G    S    D    V    D    S    I    A    V    G    S    G    T    K    F 819             828             837             846             855             864
TGC  AGT  GGC  TCC  TGG  GAT  AAG  ATG  CTA  AAG  ATC  TGG  TCT  ACA  GTC  CCT  ACA  GAT
 C    S    G    S    W    D    K    M    L    K    I    W    S    T    V    P    T    D 873             882             891             900             909             918
GAA  GAT  GAT  GAA  ATG  GAG  GAG  TCC  ACA  AAT  CGA  CCA  AGA  AAG  CAG  AAG  ACA
 E    D    D    E    M    E    E    S    T    N    R    P    R    K    Q    K    T 927             936             945             954             963             972
GAA  CAG  TTG  GGA  CTA  ACA  AGG  ACT  CCC  ATA  GTG  ACC  CTC  TCT  GGC  CAC  ATG  GAG
 E    Q    L    G    L    T    R    T    P    I    V    T    L    S    G    H    M    E 981             990             999            1008            1017            1026
GCA  GTT  TCC  TCA  GTT  CTG  TGG  TCA  GAT  GCT  GAA  GAA  ATC  TGC  AGT  GCA  TCT  TGG
 A    V    S    S    V    L    W    S    D    A    E    E    I    C    S    A    S    W
```

```
                1035            1044            1053            1062            1071            1080
GAC CAT ACA ATT AGA GTG TGG GAT GTT GAG TCT GGC AGT CTT AAG TCA ACT TTG
 D   H   T   I   R   V   W   D   V   E   S   G   S   L   K   S   T   L 1089            1098            1107            1116            1125            1134
ACA GGA AAT AAA GTG TTT AAT TGT ATT TCC TAT TCT CCA CTT TGT AAA CGT TTA
 T   G   N   K   V   F   N   C   I   S   Y   S   P   L   C   K   R   L 1143            1152            1161            1170            1179            1188
GCA TCT GGA AGC ACA GAT AGG CAT ATC AGA CTG TGG GAT CCC CGA ACT AAA GAT
 A   S   G   S   T   D   R   H   I   R   L   W   D   P   R   T   K   D 1197            1206            1215            1224            1233            1242
GGT TCT TTG GTG TCG CTG TCC CTA ACG TCA CAT ACT GGT TGG GTG ACA TCA GTA
 G   S   L   V   S   L   S   L   T   S   H   T   G   W   V   T   S   V 1251            1260            1269            1278            1287            1296
AAA TGG TCT CCT ACC CAT GAA CAG CAG CTG ATT TCA GGA TCT TTA GAT AAC ATT
 K   W   S   P   T   H   E   Q   Q   L   I   S   G   S   L   D   N   I 1305            1314            1323            1332            1341            1350
GTT AAG CTG TGG GAT ACA AGA AGT TGT AAG GCT CCT CTC TAT GAT CTG GCT GCT
 V   K   L   W   D   T   R   S   C   K   A   P   L   Y   D   L   A   A

FIGURE 1D
```

```
      1359              1368              1377      1386              1395              1404
CAT GAA GAC AAA GTT CTG AGT GTA GAC TGG ACA GAC ACA GGG CTA CTT CTG AGT
 H   E   D   K   V   L   S   V   D   W   T   D   T   G   L   L   L   S 1413              1422              1431      1440              1449              1458
GGA GGA GCA GAC AAT AAA TTG TAT TCC TAC AGA TAT TCA CCT ACC ACT TCC CAT
 G   G   A   D   N   K   L   Y   S   Y   R   Y   S   P   T   T   S   H 1467              1476              1485      1494              1503              1512
GTT GGG GCA TGA AAG TGA ACA ATA ATT TGA CTA TAG AGA TTA TTT CTG TAA ATG
 V   G   A 1521              1530              1539      1548              1557              1566
AAA TTG GTA GAG AAC CAT GAA ATT ACA TAG ATG CAG ATG CAG AAA GCA GCC TTT 1575              1584              1593      1602              1611              1620
TGA AGT TTA TAT AAT GTT TTC ACC CTT CAT AAC AGC TAA CGT ATC ACT TTT TCT 1629              1638              1647      1656              1665              1674
TGA AGT TTA TAT AAT GTT TTC ACC CTT CAT AAC AGC TAA CGT ATC ACT TTT TCT 1629              1638              1647      1656              1665              1674
TAT TTT GTA TTT ATA ATA AGA TAG GTT GTG TTT ATA AAA TAC AAA CTG TGG CAT 1683              1692              1701      1710              1719              1728
ACA TTC TCT ATA CAA ACT TGA AAT TAA ACT GAG TTT TAC ATT TCT CTT TAA AAA
```

FIGURE 1E

```
       1737           1746           1755           1764           1773           1782
AAA AAA AAG ATT AAG GAA AAA AGG TGA TAT GGA AAC CTA GTG GGG AAT TTA ACG
       1791           1800           1809           1818           1827           1836
GTA AAT AGA AGG GGG GCC GTT CTG GGG GGT CCA TCT TTT AGG TAC GCG GGA TTG
       1845           1854           1863           1872           1881           1890
CGG GGT CCT AGC TCT CTC TAG GGG GTC CCC AAT TTC AGA TCA GGG GGG GGT GGT
       1899           1908           1917           1926           1935           1944
TTT AAA GGT GCG GGG CTT GGG GAA ACC CTG GGG GTT TCC CAA TTT TAA GGG CCT
       1953           1962           1971           1980           1989           1998
TTG GGG GGA ATT TCC CCT TTT TGG CAC AAT GGG GGG GTT ATT GCC GGA AGG GCG
       2007           2016           2025           2034           2043           2052
CCC CCA CCG GTT GGC CCC GTC TCC AAA AAT TTG GGG GGC CCC TGA AGG GGG GAG
       2061           2070           2079           2088           2097
TTG GGG CGG CGC CCC TTT TAG GGG GCG GTT TAT ATG GCC GGG GGG GGG   3'
```

FIGURE 1F

```
  1  MA------QLQTRFYTDNKK--YAVDDVPFSIPAASEIADLS    1312429
  1  MTEDKSQVKIRFFTREKDELLHVQDTPMYAPISLKRYGLS       gi|1928989

35  NINKLLKDKNEFHKHVEFDFLIKGQFLRMPLDKHMEMEN        1312429
 41  EIVNHLLGS---EKPVPFDFLIEGELLRTSLHDYLTKKG        gi|1928989

75  VSSEEVVEIEYVEKYTAPQPEQCMFHDDWISSIKGAEEW-       1312429
 77  LSSEASLNVEYTRAILPPSYLNSFSNEDWVSSLDVGDGSK       gi|1928989

114  -ILTGSYDKTSRIWSLEGKSIMTIVGHTDVVKDVAWVKKD       1312429
117  HIISGSYDGIVRTWDLSGNVQKQYSGHSGPIRAVKYISNT       gi|1928989

153  SLSCLLLSASMDQTILLWEWNVERNKV-----------         1312429
157  RL----VSAGNDRTLRLWKTKNDDLKLTSQQQAQEDDDDE       gi|1928989

180  ------KALHCCRGHAGSVDSIAVDGSGTKFCSGSWDKML       1312429
193  VNIEDGKTLAILEGHKAPVVSIDVSDNSRIL-SASYDNSI       gi|1928989

214  KIWSTV-----PTDEEDEMEESTNR-----PRKKQKTEQLG      1312429
232  GFWSTIYKEMTVVDPLEDINNPNNKISTAARKRKKLTMKD       gi|1928989

245  LT---RTPIVTLSGHMEAVSSVLWSDAEEI--CSASWDHT       1312429
272  GTIRRRAPLSLLESHTAPVEQVIFDSTDNTVGYSVSQDHT       gi|1928989
```

FIGURE 2A

```
280  IRVWDVESGS-LKSTLTGNKVFNCISYSPLCKRLASGSTD     1312429
312  IKTWDLVTARCIDTRTTSYSLLSIAQLSTL-NLLACGSSA     gi1928989

319  RHIRLWDPRTKDGSLVSLS-LTSHTGWVTSVKWSPTHEQQ     1312429
351  RHITLHDPRVGASSKVTQQQLIGHKNFVSSLDTCPENEYI     gi1928989

358  LISGSLDNIVKLWDTRSCKAPLYDLAAHE----DKV       1312429
391  LCSGSHDGTVKVWDVRS-TSPMYTITREDKSVQKGVNDKV    gi1928989

390  LSVDWTDTGLLSGGADNKLYSYRYSPTTSHVGA          1312429
430  FAVKWAEKVGIISAGQDKKI---QINKGDNIFKN         gi1928989
```

MICROTUBULE-ASSOCIATED PROTEIN

FIELD OF THE INVENTION

This invention relates to nucleic acid and amino acid sequences of a human microtubule-associated protein and to the use of these sequences in the diagnosis, treatment, and prevention of diseases associated with immune disorders and cancer.

BACKGROUND OF THE INVENTION

Microtubules (MTs) are involved in many cellular functions such as mitosis, morphogenesis, motility, and intracellular organelle transport. For example, disruption of MTs by various MT-destabilizing agents results in major changes in cytoplasmic organization, including collapse of intermediate filaments and redistribution of the Golgi apparatus and endoplasmic reticulum. MTs also function in the maintenance of cell shape, movement of eukaryotic cilia and flagella, formation of the mitotic spindle, and regulation of organelle distribution and vesicle movements. Regulation of the dynamic properties of MTs is believed to play a role in many of these functions.

A group of proteins that bind MTs are defined as microtubule-associated proteins (MAPs). MAPS are involved in modulating MT dynamics and function. MAPs can be categorized into two major classes according to their primary function; motor proteins, which include the kinesin superfamily and the dynein family, and non-motor proteins, which are further divided into the high molecular weight MAPs, including MAP1A, MAP1B, MAP2, and MAP4 and the low molecular weight tau proteins. (See, e.g., Ding M. Et al. (1996) J. Biol. Chem. 271:12555–12561.) Among the identified functions of MAPs in neuronal cells, kinesin and cytoplasmic dynein are responsible for anterograde and retrograde axonal transport, respectively. Tau protein and MAP2 appear to be required for initial neurite growth. It is well known that the function of MAPs can be regulated through phosphorylation. For example, phosphorylation of MAPs can alter their affinity for MTs in vivo and affect their ability to stabilize MTs.

Hyperphosphorylated microtubule-associated protein tau is the major proteinaceous component of paired helical and, straight filaments which constitute a defining neuropathological characteristic of Alzheimer's disease and a number of other neurodegenerative disorders. Full length tau protein can assemble into Alzheimer-like filaments upon incubation with heparin, a repeating disaccharide chain. Heparin also promotes phosphorylation of tau protein by a number of kinases, prevents tau protein from binding to taxol-stabilized microtubules, and produces rapid disassembly of microtubules assembled from tau protein and tubulin. Moreover, cAMP-dependent protein kinase and $Ca^{2+}$/calmodulin-dependent protein kinase II phosphorylate tau proteins at specific sites in vitro, some of which are also phosphorylated in PHF-tau. Hyperphosphorylation of tau protein results in its inability to bind to microtubules and is believed to precede paired helical filament assembly. Phosphorylation-independent interaction between recombinant tau protein and sulfated glycosaminoglycans leads to the formation of Alzheimer-like filaments under physiological conditions in vitro. (See e.g., Hasegawa, M. Et al. (1997) J. Biol. Chem. 272:33118–33124.)

The discovery of a new human microtubule-associated protein and the polynucleotides encoding it satisfies a need in the art by providing new compositions which are useful in the diagnosis, treatment, and prevention of diseases associated with cell proliferation.

SUMMARY OF THE INVENTION

The invention features a substantially purified polypeptide, human microtubule-associated protein (HMAP), comprising a sequence of SEQ ID NO:1 or a fragment of SEQ ID NO:1.

The invention further provides a substantially purified variant of HMAP having at least 90% amino acid identity to the sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide identity to the polynucleotide encoding the polypeptide comprising the sequence of SEQ ID NO:1 or a fragment of SEQ ID NO:1.

Additionally, the invention provides a composition comprising a polynucleotide encoding the polypeptide comprising the sequence of SEQ ID NO:1 or a fragment of SEQ ID NO:1. The invention further provides an isolated and purified polynucleotide which hybridizes under stringent conditions to the polynucleotide encoding the polypeptide comprising the sequence of SEQ ID NO:1 or a fragment of SEQ ID NO:1, as well as an isolated and purified polynucleotide which is complementary to the polynucleotide encoding the polypeptide comprising the sequence of SEQ ID NO:1 or a fragment of SEQ ID NO:1.

The invention also provides an isolated and purified polynucleotide comprising a sequence of SEQ ID NO:2 or a fragment of SEQ ID NO:2, and an isolated and purified polynucleotide variant having at least 90% polynucleotide identity to the polynucleotide comprising the sequence of SEQ ID NO:2 or a fragment of SEQ ID NO:2. The invention also provides an isolated and purified polynucleotide which is complementary to the polynucleotide comprising the sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising a sequence of SEQ ID NO:1 or a fragment of SEQ ID NO:1, the method comprising the steps of: (a) culturing the host cell containing an expression vector containing at least a fragment of a polynucleotide encoding HMAP under conditions suitable for the expression of the polypeptide; and (b) recovering the polypeptide from the host cell culture.

The invention also provides a pharmaceutical composition comprising a substantially purified HMAP having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist to HMAP.

The invention also provides a method for treating or preventing an immune disorders, the method comprising administering to a subject in need of such treatment an effective amount of an antagonist to HMAP.

The invention also provides a method for detecting a polynucleotide encoding HMAP in a biological sample containing nucleic acids, the method comprising the steps of: (a) hybridizing the complement of the polynucleotide encoding the polypeptide comprising the sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding HMAP in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HMAP. The alignment was produced using MacDNASIS PRO™ software (Hitachi Software Engineering Co. Ltd., San Bruno, Calif.).

FIGS. 2A and 2B show the amino acid sequence alignments among HMAP (1312429; SEQ ID NO:1) and microtubule-associated protein from Saccharomyces cervisiae (GI 1928989; SEQ ID NO:3), produced using the multisequence alignment program of DNASTAR™ software (DNASTAR Inc, Madison Wis.).

DESCRIPTION OF THE INVENTION

Figure 3A:
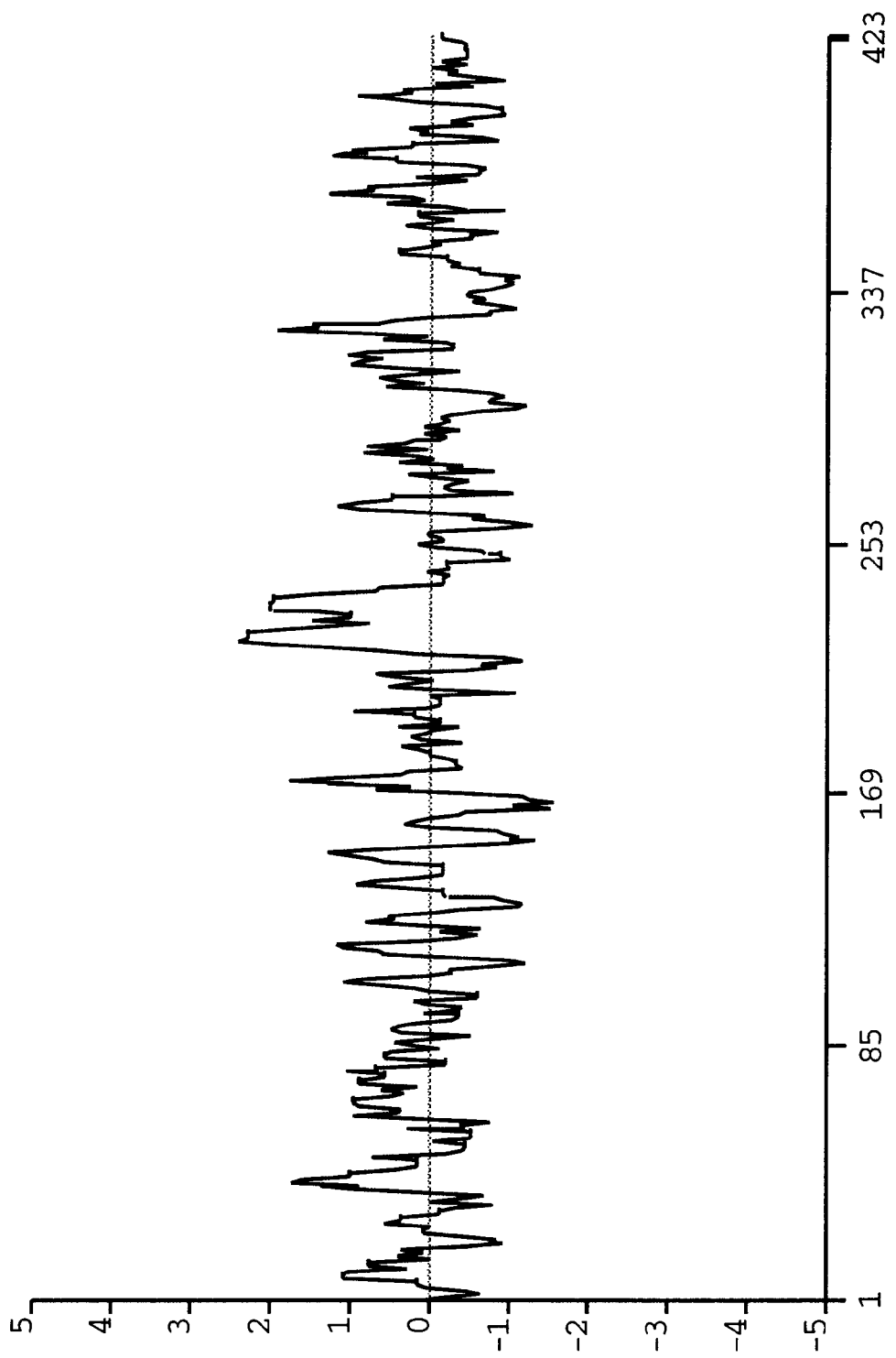
FIGS. 3A and 3B show the hydrophobicity plots for HMAP, SEQ ID NO:1 and microtubule-associated protein form S. Cervisiae (SEQ ID NO:3), respectively; the positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HMAP," as used herein, refers to the amino acid sequences of substantially purified HMAP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HMAP, increases or prolongs the duration of the effect of HMAP. Agonists may include proteins, nucleic acids, carbohydrates, or any other molecules which bind to and modulate the effect of HMAP.

An "allele" or an "allelic sequence," as these terms are used herein, is an alternative form of the gene encoding HMAP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HMAP, as described herein, include those sequences with deletions, insertions, or substitutions of different nucleotides, resulting in a polynucleotide the same HMAP or a polypeptide with at least one functional characteristic of HMAP. Included within this definition are polymorphisms which may or may not be readily detectable using a particular oligonucleotide probe of the polynucleotide encoding HMAP, and improper or unexpected hybridization to alleles, with a locus other than the normal chromosomal locus for the polynucleotide sequence encoding HMAP. The encoded protein may also be "altered," and may contain deletions, insertions, or substitutions of amino acid residues which produce a silent change and result in a functionally equivalent HMAP. Deliberate amino acid substitutions may be made on the basis of similarity in polarity, charge, solubility, hydrophobicity, hydrophilicity, and/or the amphipathic nature of the residues, as long as the biological or immunological activity of HMAP is retained. For example, negatively charged amino acids may include aspartic acid and glutamic acid, positively charged amino acids may include lygine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HMAP which are preferably about to about 15 amino acids in length and which retain some biological activity or immunological activity of HMAP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer,* a *Laboratory Manual*, Cold Spring Harbor Press, Plainview, N.Y., pp. 1–5.)

The term "antagonist," as it is used herein, refers to a molecule which, when bound to HMAP, decreases the amount or the duration of the effect of the biological or immunological activity of HMAP. Antagonists may include proteins, nucleic acids, carbohydrates, antibodies, or any other molecules which decrease the effect of HMAP.

As used herein, the term "antibody" refers to intact molecules as well as to fragments thereof, such as Fab, F(ab')$_2$, and Fv fragments, which are capable of binding the epitopic determinant. Antibodies that bind HMAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HMAP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HMAP or fragments of HMAP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HMAP, by northern analysis is indicative of the presence of nucleic acids encoding HMAP in a sample, and thereby correlates with expression of the transcript from the polynucleotide encoding HMAP.

A "deletion," as the term is used herein, refers to a change in the amino acid or nucleotide sequence that results in the absence of one or more amino acid residues or nucleotides.

The term "derivative," as used herein, refers to the chemical modification of HMAP, of a polynucleotide sequence encoding HMAP, or of a polynucleotide sequence complementary to a polynucleotide sequence encoding HMAP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign program (Lasergene software package, DNASTAR, Inc., Madison Wis.). The MegAlign program can create alignments between two or more sequences according to different methods, e.g., the Clustal Method. (Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) Methods in Enzymology 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HMAP. For example, modulation may cause an increase or a decrease in protein activity, binding characteristics, or any other biological, functional, or immunological properties of HMAP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HMAP, or fragments thereof, or HMAP itself may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HMAP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human microtubule-associated protein (HMAP), the polynucleotides encoding HMAP, and the use of these compositions for the diagnosis, treatment, or prevention of immune disorders and cancer.

Nucleic acids encoding the HMAP of the present invention were first identified in Incyte Clone 1312429 from the bladder tumor cDNA library (BLADTUT02) using a computer search for amino acid sequence alignments. A consensus sequence, SEQ ID NO:2, was derived from the following overlapping and/or extended nucleic acid sequences: Incyte Clones 1312429 (BLADTUT02), 2368182 and 2368151 (ADRENOT07), 3519656 (LUNGNON03), 3730457 (SMCCNON03), 1260511 (SYNORAT05), 216842 (STOMNOT01), and 1214331 (BRSTTUT01).

Figure 3B:
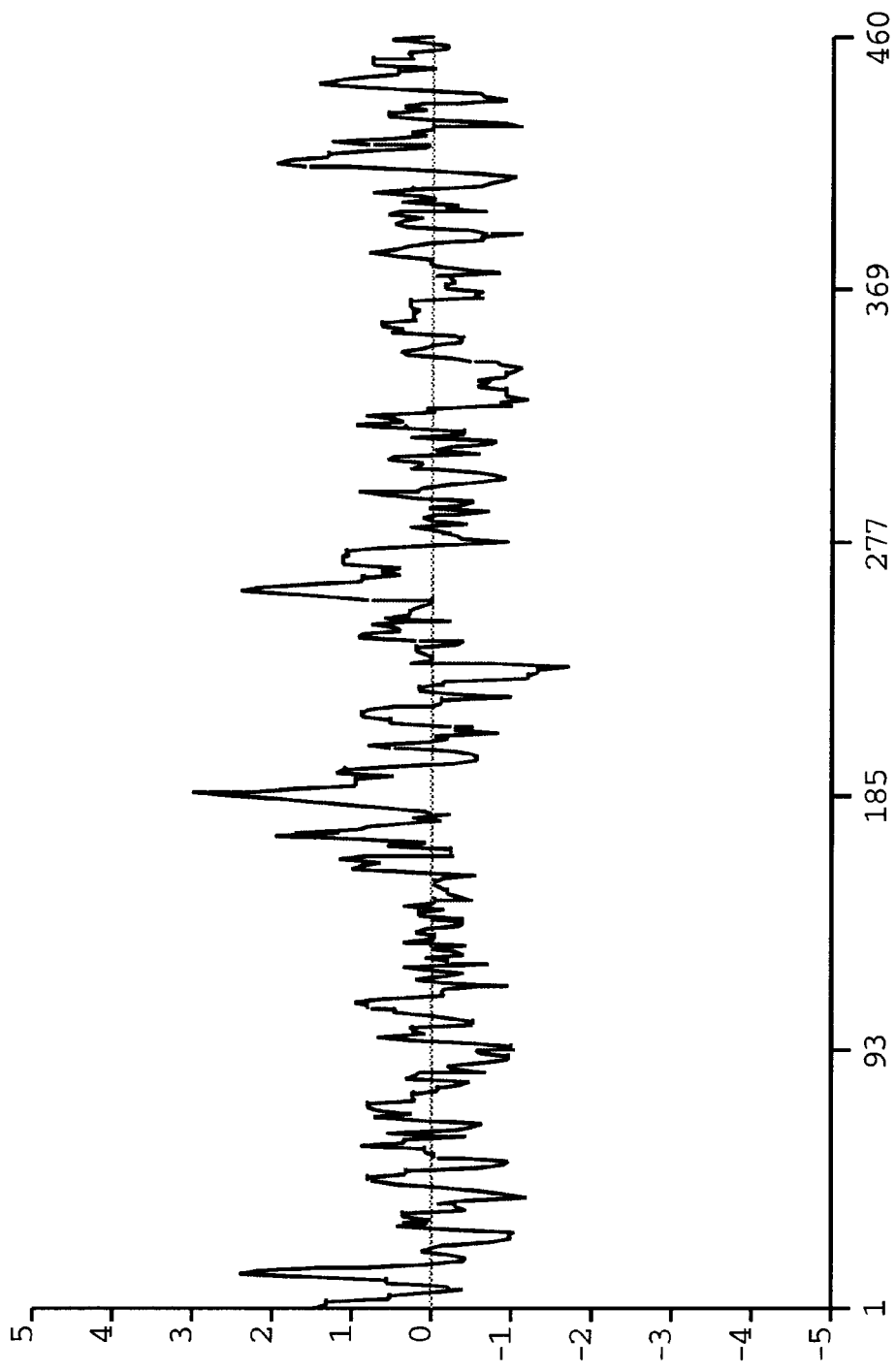

In one embodiment, the invention encompasses a polypeptide comprising the amino acid sequence of SEQ ID NO:1, as shown in FIGS. 1A, 1B, 1C, 1D, 1E, and 1F. HMAP is 423 amino acids in length and has one potential cAMP- and cGMP-dependent protein kinase phosphorylation site at residue $S_{153}$; three potential casein kinase II phosphorylation sites at residues $S_{106}$, $T_{122}$, and $S_{266}$; nine potential protein kinase C phosphorylation sites at residues $S_{106}$, $T_{122}$, $T_{231}$, $T_{279}$, $S_{289}$, $T_{317}$, $S_{347}$, $S_{374}$, and $S_{411}$; one potential tyrosine kinase phosphorylation site at residue $R_7$; and two potential beta-transduction family trp-asp repeats signature sites begining at residues I127, and $L_{358}$ in which $W_{276}D$ and $W_{370}D$ are the trp-asp repeat motifs. As shown in FIGS. 2A and 2B, HMAP has chemical and structural homology with microtubule-associated protein form S. Cerevisiae (GI 1928989; SEQ ID NO:3) and the $W_{370}D$ repeat domain. In particular, HMAP and microtubule-associated protein from S. cervisiae share 32% identity. As illustrated by FIGS. 3A and 3B, HMAP and microtubule-associated protein from S. cervisiae have rather similar hydrophobicity plot. A useful fragment of the nucleic acid sequence (SEQ ID NO:2) is from about $C_{316}$–$C_{343}$ and $T_{451}$–$C_{472}$. Northern analysis shows the expression of this sequence in various libraries, at least 63% of which are immortalized or cancerous and at least 21% of which involve the immune response.

The invention also encompasses HMAP variants. A preferred HMAP variant is one which has at least about 80%, more preferably at least about 90%, and most preferably at least about 95% amino acid sequence identity to the HMAP amino acid sequence, and which contains at least one functional or structural characteristic of HMAP.

The invention also encompasses polynucleotides which encode HMAP. In a particular embodiment, the invention encompasses a polynucleotide sequence comprising the sequence of SEQ ID NO:2, which encodes an HMAP.

The invention also encompasses a variant of a polynucleotide sequence encoding HMAP. In particular, such a variant polynucleotide sequence will have at least about 80%, more preferably at least about 90%, and most preferably at least about 95% polynucleotide sequence identity to the polynucleotide sequence encoding HMAP. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HMAP.

It will be appreciated by those skilled in the art that as a result of the degeneracy of the genetic code, a multitude of polynucleotide sequences encoding HMAP, some bearing minimal homology to the polynucleotide sequences of any known and naturally occurring gene, may be produced.

Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HMAP, and all such variations are to be considered as being specifically disclosed.

Although nucleotide sequences which encode HMAP and its variants are preferably capable of hybridizing to the nucleotide sequence of the naturally occurring HMAP under appropriately selected conditions of stringency, it may be advantageous to produce nucleotide sequences encoding HMAP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HMAP and its derivatives without altering the encoded amino acid sequences include the production of RNA transcripts having more desirable properties, such as a greater half-life, than transcripts produced from the naturally occurring sequence.

The invention also encompasses production of DNA sequences which encode HMAP and HMAP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HMAP or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (U.S. Biochemical Corp., Cleveland, Ohio), Taq polymerase (Perkin Elmer), thernostable $T_7$ polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the Hamilton Micro Lab 2200 (Hamilton, Reno, Nev.), Peltier Thermal Cycler (PTC200; M J Research, Watertown, Mass.) and the ABI Catalyst and 373 and 377 DNA Sequencers (Perkin Elmer).

The nucleic acid sequences encoding HMAP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer complementary to a linker sequence within the vector and a primer specific to the region predicted to encode the gene. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HMAP may be used in recombinant DNA molecules to direct expression of HMAP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HMAP.

As will be understood by those of skill in the art, it may be advantageous to produce HMAP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HMAP-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HMAP may be ligated to a heterologous sequence to encode a fusion protein. For example, to screen peptide libraries for inhibitors of HMAP activity, it may be useful to encode a chimeric HMAP protein that can be recognized by a commercially available antibody. A fusion protein may also be engineered to contain a cleavage site located between the HMAP encoding sequence and the heterologous protein sequence, so that HMAP may be cleaved and purified away from the heterologous moiety.

In another embodiment, sequences encoding HMAP may be synthesized, in whole or in part, using chemical methods well known in the art. (See, e.g., Caruthers, M. H. et al. (1980) Nucl. Acids Res. Symp. Ser. 7:251–223, and Horn, T. et al. (1980) Nucl. Acids Res. Symp. Ser. 7:225–232.) Alternatively, the protein itself may be produced using chemical methods to synthesize the amino acid sequence of HMAP, or a fragment thereof. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer).

The newly synthesized peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties*, WH Freeman and Co., New York, N.Y.) Additionally, the amino acid sequence of HMAP, or any part thereof, may be altered during direct synthesis and/or combined with sequences from other proteins, or any part thereof, to produce a variant polypeptide.

In order to express a biologically active HMAP, the nucleotide sequences encoding HMAP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HMAP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HMAP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HMAP which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif.) or pSportl™ plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HMAP, vectors based on SV40 or EBV may be used with an appropriate selectable marker.

In bacterial systems, a number of expression vectors may be selected depending upon the use intended for HMAP. For example, when large quantities of HMAP are needed for the lo induction of antibodies, vectors which direct high level expression of fusion proteins that are readily purified may be used. Such vectors include, but are not limited to, multi-functional *E. coli* cloning and expression vectors such as Bluescript® (Stratagene), in which the sequence encoding HMAP may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HMAP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HMAP. For example, in one such system, *Autographa californica* nuclear polyhedrosis virus (AcNPV) is used as a vector to express foreign genes in *Spodoptera frugiperda* cells or in Trichoplusia larvae. The sequences encoding HMAP may be cloned into a non-essential region of the virus, such as the polyhedrin gene, and placed under control of the polyhedrin promoter. Successful insertion of sequences encoding HMAP will render the polyhedrin gene inactive and produce recombinant virus lacking coat protein. The recombinant viruses may then be used to infect, for example, *S. frugiperda* cells or Trichoplusia larvae in which HMAP may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HMAP may be ligated into an adenovirus transcription/translation complex consisting of the late promoter and tripartite leader sequence. Insertion in a non-essential E1 or E3 region of the viral genome may be used to obtain a viable virus which is capable of expressing HMAP in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HMAP. Such signals include the ATG initiation codon and adjacent sequences. In cases where sequences encoding HMAP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HMAP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes-and adenine phosphoribosyltransferase genes, which can be employed in tk$^-$ or apr$^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Recently, the use of visible markers has gained popularity with such markers as anthocyanins, β glucuronidase and its substrate GUS, luciferase and its substrate luciferin. Green fluorescent proteins (GFP) (Clontech, Palo Alto, Calif.) are also used (See, e.g., Chalfie, M. et al. (1994) Science 263:802–805.) These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HMAP is inserted within a marker gene sequence, transformed cells containing sequences encoding HMAP can be identified by the absence of marker gene function. Alternatively, a marker gene can be placed in tandem with a sequence encoding HMAP under the control of a single promoter. Expression of the marker gene in response to induction or selection usually indicates expression of the tandem gene as well.

Alternatively, host cells which contain the nucleic acid sequence encoding HMAP and express HMAP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HMAP can be detected by DNA-DNA or DNA-RNA hybridization or amplification using probes or fragments or fragments of polynucleotides encoding HMAP. Nucleic acid amplification based assays involve the use of oligonucleotides or oligomers based on the sequences encoding HMAP to detect transformants containing DNA or RNA encoding HMAP.

A variety of protocols for detecting and measuring the expression of HMAP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HMAP is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HMAP include oligolabeling, nick translation, end-labeling, or PCR amplification using a labeled nucleotide. Alternatively, the sequences encoding HMAP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Minn.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HMAP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HMAP may be designed to contain signal sequences which direct secretion of HMAP through a prokaryotic or eukaryotic cell membrane. Other constructions may be used to join sequences encoding HMAP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HMAP encoding sequence may be used to facilitate purification. One such expression vector provides for expression of a fusion protein containing HMAP and a nucleic acid encoding 6 histidine residues preceding a thioredoxin or an enterokinase cleavage site. The histidine residues facilitate purification on immobilized metal ion affinity chromatography. (IMIAC) (See, e.g., Porath, J. et al. (1992) Prot. Exp. Purif. 3: 263–281.) The enterokinase cleavage site provides a means for purifying HMAP from the fusion protein. (See, e.g., Kroll, D. J. et al. (1993) DNA Cell Biol. 12:441–453.)

Fragments of HMAP may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the Applied Biosystems 431A peptide synthesizer (Perkin Elmer). Various fragments of HMAP may be synthesized separately and then combined to produce the full length molecule.

THERAPEUTICS

Chemical and structural homology exists between HMAP and microtubule-associated protein from *S. Cerevisiae* (GI1928989). In addition, HMAP is in tissues associated with immune disorders and cancer. Therefore, HMAP appears to play a role in immune response and cancer.

Therefore, in one embodiment, an antagonist of HMAP or a fragment or derivative thereof may be administered to a subject to treat or prevent a cancer. Such cancers may include, but are not limited to, adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HMAP may be used directly as an antagonist or indirectly as a targeting or delivery mechanism for bringing a pharmaceutical agent to cells or tissues which express HMAP.

In another embodiment, a vector expressing the complement of the polynucleotide encoding HMAP may be administered to a subject to treat or prevent a cancer including, but not limited to, those described above.

Therefore, in another embodiment, an antagonist of HMAP may be administered to a subject to prevent or treat an immune disorder. Immune disorders may include, but are not limited to AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds HMAP may be used directly as an antagonist or indirectly as a targeting or delivery mechanism for bringing a pharmaceutical agent to cells or tissues which express HMAP.

In another embodiment, a vector expressing the complement of the polynucleotide encoding HMAP may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HMAP may be produced using methods which are generally known in the art. In particular, purified HMAP may be used to produce antibodies or to screen libraries of pharmaceutical agents to identify those which specifically bind HMAP. Antibodies to HMAP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HMAP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HMAP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HMAP amino acids may be fused with those of another protein, such as KLH, and antibodies to the chimeric molecule may be produced.

Monoclonal antibodies to HMAP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HMAP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HMAP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HMAP and its specific antibody. A two-site, monoclonal-based immunoassay utilizing monoclonal antibodies reactive to two non-interfering HMAP epitopes is preferred, but a competitive binding assay may also be employed. (Maddox, supra.)

In another embodiment of the invention, the polynucleotides encoding HMAP, or any fragment or complement thereof, may be used for therapeutic purposes. In one aspect, the complement of the polynucleotide encoding HMAP may be used in situations in which it would be desirable to block the transcription of the mRNA. In particular, cells may be transformed with sequences complementary to polynucleotides encoding HMAP. Thus, complementary molecules or fragments may be used to modulate HMAP activity, or to achieve regulation of gene function. Such technology is now well known in the art, and sense or antisense oligonucleotides or larger fragments can be designed from various locations along the coding or control regions of sequences encoding HMAP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HMAP. (See, e.g., Sambrook, supra; and Ausubel, supra.)

Genes encoding HMAP can be turned off by transforming a cell or tissue with expression vectors which express high levels of a polynucleotide, or fragment thereof, encoding HMAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HMAP. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HMAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HMAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HMAP, antibodies to HMAP, and mimetics, agonists, antagonists, or inhibitors of HMAP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HMAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HMAP or fragments thereof, antibodies of HMAP, and agonists, antagonists or inhibitors of HMAP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HMAP may be used for the diagnosis of disorders characterized by expression of HMAP, or in assays to monitor patients being treated with HMAP or agonists, antagonists, or inhibitors of HMAP. Antibodies useful for diagnostic purposes may be prepared in the same manner as described above for therapeutics. Diagnostic assays for HMAP include methods which utilize the antibody and a label to detect HMAP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HMAP, including ELISAs, RIAs, and FACS, are known in the art and provide a basis for diagnosing altered or abnormal levels of HMAP expression. Normal or standard values for HMAP expression are established by combining body fluids or cell extracts taken from normal mammalian subjects, preferably human, with antibody to HMAP under conditions suitable for complex formations. The amount of standard complex formation may be quantitated by various methods, preferably by photometric means. Quantities of HMAP expressed in subject samples, control and disease from biopsied tissues are compared with the standard values. Deviation between standard and subject values establishes the parameters for diagnosing disease.

In another embodiment of the invention, the polynucleotides encoding HMAP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HMAP may be correlated with disease. The diagnostic assay may be used to determine absence, presence, and excess expression of HMAP, and to monitor regulation of HMAP levels during therapeutic intervention.

In one aspect, hybridization with PCR probes which are capable of detecting polynucleotide sequences, including genomic sequences, encoding HMAP or closely related molecules may be used to identify nucleic acid sequences which encode HMAP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HMAP, alleles, or related sequences.

Probes may also be used for the detection of related sequences, and should preferably contain at least 50% of the nucleotides from any of the HMAP encoding sequences. The hybridization probes of the subject invention may be DNA or RNA and may be derived from the sequence of SEQ ID NO:2 or from genomic sequences including promoters, enhancers, and introns of the HMAP gene.

Means for producing specific hybridization probes for DNAs encoding HMAP include the cloning of polynucleotide sequences encoding HMAP or HMAP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HMAP may be used for the diagnosis of a disorder associated with expression of HMAP. Examples of such a disorder include, but are not limited to, cancers such as adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. The polynucleotide sequences encoding HMAP may be used in Southern or northern analysis, dot blot, or other membrane-based technologies; in PCR technologies; or in dipstick, pin, ELISA assays or microarrays utilizing fluids or tissues from patient biopsies to detect altered HMAP expression. Such qualitative or quantitative methods are well known in the art. The polynucleotide sequences encoding HMAP may be used in Southern or northern analysis, dot blot, or other membrane-based technologies; in PCR technologies; in dipstick, pin, and ELISA assays; and in microarrays utilizing fluids or tissues from patients to detect altered HMAP expression. Such qualitative or quantitative methods are well known in the art.

In a particular aspect, the nucleotide sequences encoding HMAP may be useful in assays that detect the presence of associated disorders, particularly those mentioned above. The nucleotide sequences encoding HMAP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HMAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HMAP, a normal or standard profile for expression is established. This may be accomplished by combining body fluids or cell extracts taken from normal subjects, either animal or human, with a sequence, or a fragment thereof, encoding HMAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HMAP may involve the use of PCR. These oligomers may be chemically synthesized, generated enzymatically, or produced in vitro. Oligomers will preferably contain a fragment of a polynucleotide encoding HMAP, or a fragment of a polynucleotide complementary to the polynucleotide encoding HMAP, and will be employed under optimized conditions for identification of a specific gene or condition. Oligomers may also be employed under less stringent conditions for detection or quantitation of closely related DNA or RNA sequences.

Methods which may also be used to quantitate the expression of HMAP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

In one embodiment, the microarray is prepared and used according to methods known in the art. (See, e.g., Chee et al. (1995) PCT application WO95/11995; Lockhart, D. J. et al. (1996) Nat. Biotech. 14:1675–1680; and Schena, M. et al. (1996) Proc. Natl. Acad. Sci. 93:10614–10619.)

The microarray is preferably composed of a large number of unique single-stranded nucleic acid sequences, usually either synthetic antisense oligonucleotides or fragments of cDNAs. The oligonucleotides are preferably about 6 to 60 nucleotides in length, more preferably about 15 to 30 nucleotides in length, and most preferably about 20 to 25 nucleotides in length. It may be preferable to use oligonucleotides which are about 7 to 10 nucleotides in length. The microarray may contain oligonucleotides which cover the known 5' or 3' sequence, sequential oligonucleotides which cover the full length sequence, or unique oligonucleotides selected from particular areas along the length of the sequence. Polynucleotides used in the microarray may be oligonucleotides specific to a gene or genes of interest. Oligonucleotides can also be specific to one or more unidentified cDNAs associated with a particular cell type or tissue type. It may be appropriate to use pairs of oligonucleotides on a microarray. The first oligonucleotide in each pair differs from the second oligonucleotide by one nucleotide. This nucleotide is preferably located in the center of the sequence. The second oligonucleotide serves as a control. The number of oligonucleotide pairs may range from about 2 to 1,000,000.

In order to produce oligonucleotides for use on a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack secondary structure that may interfere with hybridization. In one aspect, the oligomers may be synthesized on a substrate using a light-directed chemical process. (See, e.g., Chee et al., supra.) The substrate may be any suitable solid support, e.g., paper, nylon, any other type of membrane, or a filter, chip, or glass slide.

In another aspect, the oligonucleotides may be synthesized on the surface of the substrate using a chemical coupling procedure and an ink jet application apparatus. (See, e.g., Baldeschweiler et al. (1995) PCT application WO95/251116.) An array analogous to a dot or slot blot (HYBRIDOT® apparatus, GIBCO/BRL) may be used to arrange and link cDNA fragments or oligonucleotides to the surface of a substrate using a vacuum system or thermal, UV, mechanical, or chemical bonding procedures. An array may also be produced by hand or by using available devices, materials, and machines, e.g. Brinkmann® multichannel pipettors or robotic instruments. The array may contain from 2 to 1,000,000 or any other feasible number of oligonucleotides.

In order to conduct sample analysis using the microarrays, polynucleotides are extracted from a sample. The sample may be obtained from any bodily fluid, e.g., blood, urine, saliva, phlegm, gastric juices, cultured cells, biopsies, or other tissue preparations. To produce probes, the polynucleotides extracted from the sample are used to produce nucleic acid sequences complementary to the nucleic acids on the microarray. If the microarray contains cDNAs, antisense RNAs (aRNAs) are appropriate probes. Therefore, in one aspect, mRNA is reverse-transcribed to cDNA. The cDNA, in the presence of fluorescent label, is used to produce fragment or oligonucleotide aRNA probes. The fluorescently labeled probes are incubated with the microarray so that the probes hybridize to the microarray oligonucleotides. Nucleic acid sequences used as probes can include polynucleotides, fragments, and complementary or antisense sequences produced using restriction enzymes, PCR, or other methods known in the art.

Hybridization conditions can be adjusted so that hybridization occurs with varying degrees of complementarity. A scanner can be used to determine the levels and patterns of fluorescence after removal of any nonhybridized probes. The degree of complementarity and the relative abundance of each oligonucleotide sequence on the microarray can be assessed through analysis of the scanned images. A detection system may be used to measure the absence, presence, or level of hybridization for any of the sequences. (See, e.g., Heller, R. A. et al. (1997) Proc. Natl. Acad. Sci. 94:2150–2155.)

In another embodiment of the invention, nucleic acid sequences encoding HMAP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and*

Biotechnology, VCH Publishers New York, N.Y., pp. 965–968.) Examples of genetic map data can be found in various scientific journals or at the Online Mendelian Inheritance in Man (OMIM) site. Correlation between the location of the gene encoding HMAP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HMAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HMAP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HMAP, or fragments thereof, and washed. Bound HMAP is then detected by methods well known in the art. Purified HMAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HMAP specifically compete with a test compound for binding HMAP. In this manner, antibodies can be used to detect the presence of any peptide which shares one or more antigenic determinants with HMAP.

In additional embodiments, the nucleotide sequences which encode HMAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. BLADTUT02 cDNA Library Construction

The BLADTUT02 cDNA library was constructed from cancerous bladder tissue from an 80-year-old Caucasian female who had undergone radical cystectomy following diagnosis of grade 3 (of 4) invasive transitional cell carcinoma forming a mass on the posterior wall of the bladder with extension into the trigone. The tumor was found to be deeply invasive, measuring up to 1 cm in thickness, extending to perivesical fat and extending to within 0.8 cm to the vaginal mucosal margin. Left pelvic lymph node was found negative for tumor. Patient's history included diagnoses of malignant neoplasm of uterus, benign hypertension, atherosclerosis, and atrial fibrillation. Prior to surgery, the patient had undergone bladder operation, total abdominal hysterectomy, removal of both ovaries, partial thyroidectomy, division of thyroid isthmus, aortocoronary bypass of three coronary arteries, and resection and replacement of abdominal aorta. Patient's family history included diagnoses of acute renal failure and osteoarthritis in patient's mother, and atherosclerosis in patient's father and sibling.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an SW28 rotor in a Beckman L8-70M ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were as before. The mRNA was then isolated using the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248-013, Gibco/BRL).The cDNAs were fractionated on a Sepharose CL4B column (Cat. #275105-01; Pharmacia), and those cDNAs exceeding 400 bp were ligated into pINCY 1. The plasmid pINCY 1 was subsequently transformed into DH5a™ competent cells (Cat. #18258-012; Gibco/BRL).

II. Isolation and Sequencing of cDNA Clones

Plasmid DNA was released from the cells and purified using the REAL Prep 96 Plasmid Kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III. Homology Searching of cDNA Clones and Their Deduced Proteins

After the reading-frame was determined, the nucleotide sequences of the Sequence Listing or amino acid sequences deduced from them were used as query sequences against databases such as GenBank, SwissProt, BLOCKS, and Pima II. These databases which contain previously identified and annotated sequences, were searched for regions of homology (similarity) using BLAST, which stands for Basic Local Alignment Search Tool (Altschul (1993) supra, Altschul (1990) supra).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach, as detailed in Karlin et al. (supra) and incorporated herein by reference, searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

The nucleotide sequences and/or amino acid sequences of the Sequence Listing were used to query sequences in the GenBank, SwissProt, BLOCKS, and Pima H databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HMAP occurs. Abundance and percent abundance are also reported. Abundance directly reflects the number of times a particular transcript is represented in a cDNA library, and percent abundance is abundance divided by the total number of sequences examined in the cDNA library.

V. Extension of HMAP Encoding Polynucleotides

The nucleic acid sequence of Incyte Clone 1312429 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2× Carb. The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

To produce oligonucleotides for a microarray, one of the nucleotide sequences of the present invention is examined using a computer algorithm which starts at the 3' end of the nucleotide sequence. For each, the algorithm identifies oligomers of defined length that are unique to the nucleic acid sequence, have a GC content within a range suitable for hybridization, and lack secondary structure that would interfere with hybridization. The algorithm identifies approximately 20 oligonucleotides corresponding to each nucleic acid sequence. For each sequence-specific oligonucleotide, a pair of oligonucleotides is synthesized in which the first oligonucleotides differs from the second oligonucleotide by one nucleotide in the center of the sequence. The oligonucleotide pairs can be arranged on a substrate, e.g. a silicon chip, using a light-directed chemical process. (See, e.g., Chee, supra.) In the alternative, a chemical coupling procedure and an ink jet device can be used to synthesize oligomers on the surface of a substrate. (See, e.g., Baldeschweiler, supra.) An array analogous to a dot or slot blot may also be used to arrange and link fragments or oligonucleotides to the surface of a substrate using or thermal, UV, mechanical, or chemical bonding procedures, or a vacuum system. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each oligonucleotide sequence on the microarray may be assessed through analysis of the scanned images.

VIII. Complementary Polynucleotides

Sequences complementary to the HMAP-encoding sequences, or any parts thereof, are used to detect, decrease, or inhibit expression of naturally occurring HMAP. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HMAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HMAP-encoding transcript.

IX. Expression of HMAP

Expression of HMAP is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HMAP into bacterial growth media which can be used directly in the following assay for activity.

X. Demonstration of HMAP Activity

Phosphorylation assays for HMAP (0.050 ml) are carried out at 30° C. and comprised 25 mM Tris-HCl, pH 7.4, 0.1 mM EGTA, 0.1 mM sodium orthovanadate, 2.5 uM PKI (a specific inhibitor of cyclic AMP-dependent protein kinase), protease inhibitors (0.5 mM phenylmethylsulfonyl fluoride, 5 ug/ml aprotinin, 5 ug/ml leupeptin, and 0.5 ug/ml pepstatin), HMAP (4 uM), 10 mM magnesium acetate, 2mM [gamma-$^{32}$P]ATP (approximately $10^6$ cpm/nmol), and 1 unit/ml activated p42 MAP kinase, 1 unit/ml GSK3, or 5 units/ml recombinant reconstituted neuronal cdc-2-like kinase. Glycosaminoglycans and nucleic acids are included in the assays at 50 ug/ml and tubulin at 20 uM. Reactions are initiated by addition of ATP and aliquots are removed at various times ranging from 10 minutes to 24 hours and used for SDS-polyacrylamide gel electrophoresis and immunoblotting. Alternatively, incorporation of $^{32}$P radioactivity is measured after absorption to Whatman P-81 paper. (See e.g., Hasegawa, M. Et al. (1997) J. Biol. Chem. 272:33118–33124.)

XI. Production of HMAP Specific Antibodies

HMAP substantially purified using PAGE electrophoresis (see, e.g., Harrington, M. G. (1990) Methods Enzymol. 182:488–495), or other purification techniques, is used to immunize rabbits and to produce antibodies using standard protocols. The HMAP amino acid sequence is analyzed using DNASTAR software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HMAP Using Specific Antibodies

Naturally occurring or recombinant HMAP is substantially purified by immunoaffinity chromatography using antibodies specific for HMAP. An immunoaffinity column is constructed by covalently coupling anti-HMAP antibody to an activated chromatographic resin, such as CNBr-activated Sepharose (Pharmacia & Upjohn). After the coupling, the resin is blocked and washed according to the manufacturer's instructions.

Media containing HMAP are passed over the immunoaffinity column, and the column is washed under conditions that allow the preferential absorbance of HMAP (e.g., high ionic strength buffers in the presence of detergent). The column is eluted under conditions that disrupt antibody/HMAP binding (e.g., a buffer of pH 2 to pH 3, or a high concentration of a chaotrope, such as urea or thiocyanate ion), and HMAP is collected.

XIII. Identification of Molecules Which Interact with HMAP

HMAP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HMAP, washed, and any wells with labeled HMAP complex are assayed. Data obtained using different concentrations of HMAP are used to calculate values for the number, affinity, and association of HMAP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed:

1. An isolated and purified polynucleotide encoding a human microtubule-associated protein of HMAP, said protein comprising the sequence of SEQ ID NO:1, or a fragment of SEQ ID NO:1 from about amino acid residue L358 to about amino acid residue S374.

2. A composition comprising the polynucleotide of claim 1.

3. An isolated and purified polynucleotide which is completely complementary to the polynucleotide of claim 1.

4. An isolated and purified polynucleotide comprising a sequence of SEQ ID NO:2.

5. An isolated and purified polynucleotide which is completely complementary to the polynucleotide sequence of claim 4.

6. An expression vector containing the polynucleotide of claim 1.

7. A host cell containing the expression vector of claim 6.

8. A method for producing a polypeptide, the method comprising the steps of:

(a) culturing the host cell of claim 7 under conditions suitable for the expression of the polypeptide; and (b) recovering the polypeptide from the host cell culture.

9. A method for detecting a polynucleotide encoding HMAP in a sample containing nucleic acids, the method comprising the steps of:

(a) hybridizing the polynucleotide of claim 3 to at least one of the nucleic acids of the sample, thereby forming a hybridization complex; and (b) detecting the hybridization complex, wherein the presence of the hybridization complex correlates with the presence of a polynucleotide encoding HMAP in the sample.

10. The method of claim 9 wherein the nucleic acids of the sample are amplified by the polymerase chain reaction prior to the hybridizing step.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 423 amino acids
       (B) TYPE: amino acid
       (C) STRANDEDNESS: single
       (D) TOPOLOGY: linear (vii) IMMEDIATE SOURCE:
       (A) LIBRARY: BLADTUT02
       (B) CLONE: 1312429

(xi) SEQUENCE DESCRIPTION: SEQ ID NO:1:

```
Met Ala Gln Leu Gln Thr Arg Phe Tyr Thr Asp Asn Lys Lys Tyr Ala
 1               5                  10                  15

Val Asp Asp Val Pro Phe Ser Ile Pro Ala Ala Ser Glu Ile Ala Asp
            20                  25                  30

Leu Ser Asn Ile Ile Asn Lys Leu Leu Lys Asp Lys Asn Glu Phe His
        35                  40                  45

Lys His Val Glu Phe Asp Phe Leu Ile Lys Gly Gln Phe Leu Arg Met
    50                  55                  60

Pro Leu Asp Lys His Met Glu Met Glu Asn Val Ser Ser Glu Glu Val
65                  70                  75                  80

Val Glu Ile Glu Tyr Val Glu Lys Tyr Thr Ala Pro Gln Pro Glu Gln
            85                  90                  95

Cys Met Phe His Asp Asp Trp Ile Ser Ile Lys Gly Ala Glu Glu
            100                 105                 110

Trp Ile Leu Thr Gly Ser Tyr Asp Lys Thr Ser Arg Ile Trp Ser Leu
            115                 120                 125

Glu Gly Lys Ser Ile Met Thr Ile Val Gly His Thr Asp Val Val Lys
        130                 135                 140

Asp Val Ala Trp Val Lys Lys Asp Ser Leu Ser Cys Leu Leu Leu Ser
145                 150                 155                 160

Ala Ser Met Asp Gln Thr Ile Leu Leu Trp Glu Trp Asn Val Glu Arg
            165                 170                 175

Asn Lys Val Lys Ala Leu His Cys Cys Arg Gly His Ala Gly Ser Val
            180                 185                 190

Asp Ser Ile Ala Val Asp Gly Ser Gly Thr Lys Phe Cys Ser Gly Ser
    195                 200                 205

Trp Asp Lys Met Leu Lys Ile Trp Ser Thr Val Pro Thr Asp Glu Glu
    210                 215                 220

Asp Glu Met Glu Glu Ser Thr Asn Arg Pro Arg Lys Lys Gln Lys Thr
225                 230                 235                 240

Glu Gln Leu Gly Leu Thr Arg Thr Pro Ile Val Thr Leu Ser Gly His
            245                 250                 255

Met Glu Ala Val Ser Ser Val Leu Trp Ser Asp Ala Glu Glu Ile Cys
            260                 265                 270

Ser Ala Ser Trp Asp His Thr Ile Arg Val Trp Asp Val Glu Ser Gly
        275                 280                 285

Ser Leu Lys Ser Thr Leu Thr Gly Asn Lys Val Phe Asn Cys Ile Ser
        290                 295                 300
```

```
Tyr Ser Pro Leu Cys Lys Arg Leu Ala Ser Gly Ser Thr Asp Arg His
305                 310                 315                 320

Ile Arg Leu Trp Asp Pro Arg Thr Lys Asp Gly Ser Leu Val Ser Leu
                325                 330                 335

Ser Leu Thr Ser His Thr Gly Trp Val Thr Ser Val Lys Trp Ser Pro
            340                 345                 350

Thr His Glu Gln Gln Leu Ile Ser Gly Ser Leu Asp Asn Ile Val Lys
        355                 360                 365

Leu Trp Asp Thr Arg Ser Cys Lys Ala Pro Leu Tyr Asp Leu Ala Ala
    370                 375                 380

His Glu Asp Lys Val Leu Ser Val Asp Trp Thr Asp Thr Gly Leu Leu
385                 390                 395                 400

Leu Ser Gly Gly Ala Asp Asn Lys Leu Tyr Ser Tyr Arg Tyr Ser Pro
                405                 410                 415

Thr Thr Ser His Val Gly Ala
            420
```

(2) INFORMATION FOR SEQ ID NO:2:

(i) SEQUENCE CHARACTERISTICS:
        (A) LENGTH: 2100 base pairs
        (B) TYPE: nucleic acid
        (C) STRANDEDNESS: single
        (D) TOPOLOGY: linear (vii) IMMEDIATE SOURCE:
        (A) LIBRARY: BLADTUT02
        (B) CLONE: 1312429

(xi) SEQUENCE DESCRIPTION: SEQ ID NO:2:

```
NNTAGAAGGG CAACCTCGTG CTTTCTGCAG AGGAGACCGG AGGGCAGAAG GCAGAGTCCA    60

GGCTTAGACT GCAGTTCCTC GCTTACCTGT GCAGTCTAAT TTTGAGCTGC CTCTTTGTAG   120

TCTTAAAAGG CAGGAGCTTC GTGTTGTGGG TCTGCTAACC CGTACGTTTC CGTGGGCAAG   180

TCGTGTGTAC TCCTCGCCAT GGCTCAGCTC CAAACACGCT TCTACACTGA TAACAAGAAA   240

TATGCCGTAG ATGATGTTCC CTTCTCAATC CCTGCTGCCT CTGAAATTGC CGACCTTAGT   300

AACATCATCA ATAAACTACT AAAGGACAAA AATGAGTTCC ACAAACATGT GGAGTTTGAT   360

TTCCTTATTA AGGGCCAGTT TCTGCGAATG CCCTTGGACA AACACATGGA AATGGAGAAC   420

GTCTCATCAG AAGAAGTTGT GGAAATAGAA TACGTGGAGA AGTATACTGC ACCCCAGCCA   480

GAGCAATGCA TGTTCCATGA TGACTGGATC AGTTCAATTA AAGGGCAGA GGAATGGATC   540

TTGACTGGTT CTTATGATAA GACTTCTCGG ATCTGGTCCT TGGAAGGAAA GTCAATAATG   600

ACAATTGTGG GACATACGGA TGTTGTAAAA GATGTGGCCT GGGTGAAAAA AGATAGTTTG   660

TCCTGCTTAT TATTGAGTGC TTCTATGGAT CAGACTATTC TCTTATGGGA GTGGAATGTA   720

GAGAGAAACA AAGTGAAAGC CCTACACTGC TGTAGAGGTC ATGCTGGAAG TGTAGATTCT   780

ATAGCTGTTG ATGGCTCAGG AACTAAATTT TGCAGTGGCT CCTGGGATAA GATGCTAAAG   840

ATCTGGTCTA CAGTCCCTAC AGATGAAGAA GATGAAATGG AGGAGTCCAC AAATCGACCA   900

AGAAAGAAAC AGAAGACAGA ACAGTTGGGA CTAACAAGGA CTCCCATAGT GACCCTCTCT   960

GGCCACATGG AGGCAGTTTC CTCAGTTCTG TGGTCAGATG CTGAAGAAAT CTGCAGTGCA  1020

TCTTGGGACC ATACAATTAG AGTGTGGGAT GTTGAGTCTG GCAGTCTTAA GTCAACTTTG  1080

ACAGGAAATA AAGTGTTTAA TTGTATTTCC TATTCTCCAC TTTGTAAACG TTTAGCATCT  1140

GGAAGCACAG ATAGGCATAT CAGACTGTGG GATCCCCGAA CTAAAGATGG TTCTTTGGTG  1200
```

```
TCGCTGTCCC TAACGTCACA TACTGGTTGG GTGACATCAG TAAAATGGTC TCCTACCCAT   1260

GAACAGCAGC TGATTTCAGG ATCTTTAGAT AACATTGTTA AGCTGTGGGA TACAAGAAGT   1320

TGTAAGGCTC CTCTCTATGA TCTGGCTGCT CATGAAGACA AAGTTCTGAG TGTAGACTGG   1380

ACAGACACAG GGCTACTTCT GAGTGGAGGA GCAGACAATA AATTGTATTC CTACAGATAT   1440

TCACCTACCA CTTCCCATGT TGGGGCATGA AAGTGAACAA TAATTTGACT ATAGAGATTA   1500

TTTCTGTAAA TGAAATTGGT AGAGAACCAT GAAATTACAT AGATGCAGAT GCAGAAAGCA   1560

GCCTTTTGAA GTTTATATAA TGTTTTCACC CTTCATAACA GCTAACGTAT CACTTTTTCT   1620

TATTTTGTAT TTATAATAAG ATAGGTTGTG TTTATAAAAT ACAAACTGTG GCATACATTC   1680

TCTATACAAA CTTGAAATTA AACTGAGTTT TACATTTCTC TTTAAAAAAA AAAAAAGATT   1740

AAGGAAAAAA GGTGATATGG AAACCTAGTG GGGAATTTAA CGGTAAATAG AAGGGGGGCC   1800

GTTCTGGGGG GTCCATCTTT TAGGTACGCG GGATTGCGGG GTCCTAGCTC TCTCTAGGGG   1860

GTCCCCAATT TCAGATCAGG GGGGGTGGT TTTAAAGGTG CGGGGCTTGG GGAAACCCTG    1920

GGGGTTTCCC AATTTTAAGG GCCTTTGGGG GGAATTTCCC CTTTTTGGCA CAATGGGGGG   1980

GTTATTGCCG GAAGGGCGCC CCCACCGGTT GGCCCCGTCT CCAAAAATTT GGGGGGCCCC   2040

TGAAGGGGGG AGTTGGGGCG GCGCCCCTTT TAGGGGGCGG TTTATATGGC CGGGGGGGGG   2100
```

(2) INFORMATION FOR SEQ ID NO:3:

(i) SEQUENCE CHARACTERISTICS:
        (A) LENGTH: 460 amino acids
        (B) TYPE: amino acid
        (C) STRANDEDNESS: single
        (D) TOPOLOGY: linear (vii) IMMEDIATE SOURCE:
        (A) LIBRARY: BLADTUT02
        (B) CLONE: 1312429

(xi) SEQUENCE DESCRIPTION: SEQ ID NO:3:

```
Met Thr Glu Asp Lys Ser Gln Val Lys Ile Arg Phe Phe Thr Arg Glu
 1               5                  10                  15

Lys Asp Glu Leu Leu His Val Gln Asp Thr Pro Met Tyr Ala Pro Ile
            20                  25                  30

Ser Leu Lys Arg Tyr Gly Leu Ser Glu Ile Val Asn His Leu Leu Gly
        35                  40                  45

Ser Glu Lys Pro Val Pro Phe Asp Phe Leu Ile Glu Gly Glu Leu Leu
    50                  55                  60

Arg Thr Ser Leu His Asp Tyr Leu Thr Lys Lys Gly Leu Ser Ser Glu
65                  70                  75                  80

Ala Ser Leu Asn Val Glu Tyr Thr Arg Ala Ile Leu Pro Pro Ser Tyr
                85                  90                  95

Leu Asn Ser Phe Ser Asn Glu Asp Trp Val Ser Leu Asp Val Gly
            100                 105                 110

Asp Gly Ser Lys His Ile Ile Ser Gly Ser Tyr Asp Gly Ile Val Arg
        115                 120                 125

Thr Trp Asp Leu Ser Gly Asn Val Gln Lys Gln Tyr Ser Gly His Ser
    130                 135                 140

Gly Pro Ile Arg Ala Val Lys Tyr Ile Ser Asn Thr Arg Leu Val Ser
145                 150                 155                 160

Ala Gly Asn Asp Arg Thr Leu Arg Leu Trp Lys Thr Lys Asn Asp Asp
                165                 170                 175

Leu Lys Leu Thr Ser Gln Gln Gln Ala Gln Glu Asp Asp Asp Asp Glu
```

-continued

```
              180                 185                 190
Val Asn Ile Glu Asp Gly Lys Thr Leu Ala Ile Leu Glu Gly His Lys
            195                 200                 205

Ala Pro Val Val Ser Ile Asp Val Ser Asp Asn Ser Arg Ile Leu Ser
    210                 215                 220

Ala Ser Tyr Asp Asn Ser Ile Gly Phe Trp Ser Thr Ile Tyr Lys Glu
225                 230                 235                 240

Met Thr Val Val Asp Pro Leu Glu Asp Ile Asn Asn Pro Asn Asn Lys
            245                 250                 255

Ile Ser Thr Ala Ala Arg Lys Arg Arg Lys Leu Thr Met Lys Asp Gly
            260                 265                 270

Thr Ile Arg Arg Arg Ala Pro Leu Ser Leu Leu Glu Ser His Thr Ala
        275                 280                 285

Pro Val Glu Gln Val Ile Phe Asp Ser Thr Asp Asn Thr Val Gly Tyr
        290                 295                 300

Ser Val Ser Gln Asp His Thr Ile Lys Thr Trp Asp Leu Val Thr Ala
305                 310                 315                 320

Arg Cys Ile Asp Thr Arg Thr Thr Ser Tyr Ser Leu Leu Ser Ile Ala
                325                 330                 335

Gln Leu Ser Thr Leu Asn Leu Leu Ala Cys Gly Ser Ser Ala Arg His
            340                 345                 350

Ile Thr Leu His Asp Pro Arg Val Gly Ala Ser Ser Lys Val Thr Gln
            355                 360                 365

Gln Gln Leu Ile Gly His Lys Asn Phe Val Ser Ser Leu Asp Thr Cys
    370                 375                 380

Pro Glu Asn Glu Tyr Ile Leu Cys Ser Gly Ser His Asp Gly Thr Val
385                 390                 395                 400

Lys Val Trp Asp Val Arg Ser Thr Ser Pro Met Tyr Thr Ile Thr Arg
                405                 410                 415

Glu Asp Lys Ser Val Gln Lys Gly Val Asn Asp Lys Val Phe Ala Val
            420                 425                 430

Lys Trp Ala Glu Lys Val Gly Ile Ile Ser Ala Gly Gln Asp Lys Lys
        435                 440                 445

Ile Gln Ile Asn Lys Gly Asp Asn Ile Phe Lys Asn
450                 455                 460
```